US00PP17831P2

(12) United States Plant Patent
Hofmann

(10) Patent No.: US PP17,831 P2
(45) Date of Patent: Jun. 26, 2007

(54) **NEW GUINEA *IMPATIENS* PLANT NAMED 'FISNICS BRIAM'**

(50) Latin Name: *Impatiens hawkeri*
Varietal Denomination: Fisnics Briam

(75) Inventor: Birgit Christa Hofmann, Bendorf (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 11/342,944

(22) Filed: Jan. 30, 2006

(51) Int. Cl.
*A01H 5/00* (2006.01)

(52) U.S. Cl. ..... Plt./318
(58) Field of Classification Search ..... Plt./318
See application file for complete search history.

*Primary Examiner*—Kent Bell
*Assistant Examiner*—June Hwu
(74) *Attorney, Agent, or Firm*—Yondle & Associates P.C.

(57) ABSTRACT

A new New Guinea *Impatiens* plant particularly distinguished by large, round, flat, pink to lavender-pink flowers, early flowering, uniform, medium green foliage, and a medium size plant habit that is round and bushy, is disclosed.

1 Drawing Sheet

Genus and species: *Impatiens hawkeri* W. Bull.
Variety denomination: 'Fisnics Briam'.

BACKGROUND OF THE NEW PLANT

The present invention comprises a new and distinct cultivar of New Guinea *Impatiens,* botanically known as *Impatiens hawkeri* W. Bull, and hereinafter referred to by the cultivar name 'Fisnics Briam'. The new cultivar originated from a hybridization made in the year 2002 in Hillscheid, Germany. The female parent was the proprietary pink-flowered New Guinea *Impatiens* plant '02-9152-1' (unpatented), while the male parent was the proprietary violet-pink-flowered New Guinea *Impatiens* plant '02-915-1' (unpatented). The seeds produced by the hybridization were sown in a greenhouse in Portugal in late Fall of 2002. A single plant selection was chosen for further evaluation and for asexual propagation in April 2003 in Moncarapacho, Portugal.

The new cultivar was created in 2002 in Hillscheid, Germany and has been asexually reproduced repeatedly by vegetative cuttings and tissue culture in Moncarapacho, Portugal and Hillscheid, Germany over a three-year period. 'Fisnics Brian' has not been observed under all possible environmental conditions. The present invention has been found to retain its distinctive characteristics through successive asexual propagations.

Plant Breeder's Rights for this cultivar were applied for in Switzerland on Mar. 30, 2005 and in Canada on Apr. 20, 2005.

SUMMARY OF THE INVENTION

The following are the most outstanding and distinguishing characteristics of this new cultivar when grown under normal horticultural practices in Moncarapacho. Portugal and Hillscheid, Germany.

1. A pink to lavender-pink flower color;
2. Large, round, flat-shaped flowers;
3. Uniform, medium-green foliage;
4. Medium-size, round and bushy plant habit; and
5. An early flowering response.

DESCRIPTION OF PHOTOGRAPH

This new New Guinea *Impatiens* plant is illustrated by the accompanying photograph which shows overall plant habit including blooms and foliage of the plant; the colors shown are as true as can be reasonably obtained by conventional photographic procedures. The photograph is of a whole plant about 10 weeks old, grown in a greenhouse in Hillscheid, Germany, in the Spring (May).

DESCRIPTION OF THE NEW CULTIVAR

The following detailed descriptions set forth the distinctive characteristics of 'Fisnics Briam'. The data which defines these characteristics were collected from asexual reproductions carried out in Hillscheid, Germany. The plant history was taken on 11- to 12-week old plants which were planted as rooted cuttings in 12-cm pots in late February 2005, and then grown in a greenhouse at a minimum temperature of 16° C. Color readings were taken under natural light in the greenhouse. Color references are primarily to The R.H.S. Colour Chart of The Royal Horticultural Society of London (R.H.S.) (2001).

DETAILED BOTANICAL DESCRIPTION OF THE NEW PLANT

Classification:
*Family.*—Balsaminaceae.
*Botanical.*—*Impatiens hawkeri* W. Bull.
*Common name.*—New Guinea *Impatiens.*

Parentage:
*Female parent.*—'02-9152-1' a proprietary pink-flowered New Guinea *Impatiens* plant (unpatented).
*Male parent.*—'02-915-1' a proprietary violet-pink-flowered New Guinea *Impatiens* plant (unpatented).

Growth:
*Growth and branching habit.*—Medium size, low, round, bushy, and well-branched; the growth is indeterminate, though weak after the beginning of flowering.
*Height.*—12.0 cm.
*Width.*—22.5 cm.
*Propagation.*—Terminal tips for cuttings.

*Time to production a finished flowering plant.*—9 weeks for a 12-cm pot.

*Time to initiate and develop roots.*—18 days at 22° C.

Branches:

*Average number.*—6.7.

*Length of branches.*—8 cm to 10 cm.

*Internode length.*—2.0 cm to 2.5 cm.

*Diameter of branches.*—0.5 cm to 0.7 cm.

*Stem color.*—RHS 185A (dark red) at the tips, RHS 144B (light green) at the mid part.

Leaves:

*Arrangement.*—Primarily in whorls.

*Size.*—Length: 11.8 cm. Width: 4.7 cm.

*Shape.*—Elliptic.

*Margin.*—Slightly serrate, ciliate.

*Apex.*—Acuminate.

*Base.*—Acute.

*Color* (*mature leaves*).—Upper surface: Near or somewhat deeper than RHS 137A (green). Lower surface: RHS 138B (light green).

*Color* (*immature leaves*).—Upper surface: Near RHS 137D (lighter green) for young leaves at shoot tips. Lower surface: RHS 138B (light green).

*Texture.*—Surface slightly glossy, smooth to moderately rippled or rugose faintly rippled.

*Venation color.*—Upper surface: RHS 53B near the base and lighter towards the tip. Lower surface: RHS 60A.

*Variegation.*—None.

*Petiole.*—Length: 2.0 cm. Diameter: 0.3 cm to 0.4 cm. Color: Upper surface: Near RHS 181A, may show a somewhat deeper reddish hue up to RHS 53B (same as the midrib at the base of the leaf). Lower surface: Near RHS 181A. Texture: Glabrous.

Flower buds:

*Shape.*—Ovoid.

*Size.*—Length: 2.4 cm. Width: 1.8 cm.

*Color.*—RHS 67C.

Inflorescence:

*Blooming habit* (*in spring*).—About 9 weeks after planting of rooted cuttings.

*Inflorescence type.*—Flowers appear solitary in the leaf axil of the upper nodes of the stems.

*Number of flowers per node.*—6 to 8, in various stages of development.

*Flowering season.*—Continuous mainly from March to October, depending on light intensity and temperature.

*Lastingness of individual blooms on the plant.*—About 10 days.

*Peduncle.*—Color: RHS 184A (reddish-brown). Size: Length: 5.0 cm. Diameter: 0.15 cm. Texture: Glabrous, flexible.

Flowers:

*Form of corolla.*—Single-type, 5 petals.

*Shape of corolla.*—Nearly round, with the petals overlapping and almost flat.

*Corolla size.*—Length: 7.6 cm. Width: 7.7 cm. Depth: 1.0 cm.

Petals:

*Shape.*—Cordate.

*Apex.*—Emarginate (moderately-lobed).

*Base.*—Attenuate.

*Margin.*—Entire.

*Petal size.*—Top: Length: 3.1 cm. Width: 5.2 cm. Lateral: Length: 3.9 cm. Width: 4.2 cm. Lower: Length: 4.4 cm. Width: 4.9 cm.

*Color.*—General color description: Purple-pink when opening; immediately becoming lighter and somewhat more bluish with maturity. Upper surface: Initially between RHS N57B and RHS N57C; RHS N66C to RHS 73A at maturity (pollen shed) and may thereafter turn to RHS 75A or RHS 75B; no markings. Lower surface: Initially RHS 67C, later closer to RHS 73A. Eye Zone: No distinct eye, however RHS 61C (purple-pink) in the center of the flower (under and around the androecium).

*Petal texture.*—Smooth, satiny.

*Aspect.*—Mostly flat, parallel to the surface of the foliage canopy.

Spur:

*Shape.*—Downwardly curved.

*Color.*—RHS 60A (red-purple).

*Size.*—Length: 7.0 cm. Diameter: 0.3 cm (at the flower end).

Reproductive organs:

*Stamens.*—Number: 5 fused. Stamen color (upper surface color): RHS N66C. Anthers: Fused, hooded. Pollen color: RHS 8D (yellowish-white). Pistils: Style and stigma: 5, very short, RHS 161D (yellowish). Ovary: 5-celled. Ovary length: 0.5 cm. Ovary color: RHS 187B (dark purple).

Fruit and seed set: None observed.

Disease and insect resistance: No particular resistance or susceptibility has been observed.

COMPARISON WITH PARENTAL AND COMMERCIAL CULTIVARS

'Fisnics Briam' differs from the female parent '02-9152-1' (unpatented) in that '02-9152-1' has a fuchsia eye, while 'Fisnics Briam' lacks a distinct eye zone. Additionally, 'Fisnics Briam' has a more compact plant habit than '02-9152-1'.

'Fisnics Briam' differs from the male parent '02-915-1' (unpatented), by having lighter pink flowers and a less compact but taller plant habit than '02-915-1'.

'Fisnics Briam' differs from the commercial cultivar 'Fisnics Magpink' (U.S. Plant Pat. No. 16,910) by having a uniform and more bluish-pink tone flower color, without stripes or variegation. In addition, the leaf veins of 'Fisnics Briam' show distinct reddish anthocyanin color, while the leaf veins of 'Fisnics Magpink' are colorless to partly light pink.

'Fisnics Briam' differs from the commercial cultivar 'Balcelpink' (U.S. Plant Pat. No. 14,645) by having wider leaves and a deeper foliage color. 'Fisnics Briam' has a lighter overall flower color than 'Balcelpink'. Additionally, 'Balcelpink' has a deep-pink eye, while 'Fisnics Briam' does not.

'Fisnics Briam' differs from the commercial cultivar 'Fisnics Pink' (U.S. Plant Pat. No. 13,228) by having larger flowers with a more bluish pink hue and larger leaves than 'Fisnics Pink'. Additionally, 'Fisnics Pink' has distinct purple eyes, while 'Fisnics Briam' does not.

'Fisnics Briam' differs from the commercial cultivar 'Kipas' (U.S. Plant Pat. No. 10,432) by having a flower color with a more pink hue and medium green leaves, while 'Kipas' has a more bluish hue flower color and dark green foliage.

I claim:

1. A new and distinct cultivar of New Guinea *Impatiens* plant as shown and described herein.

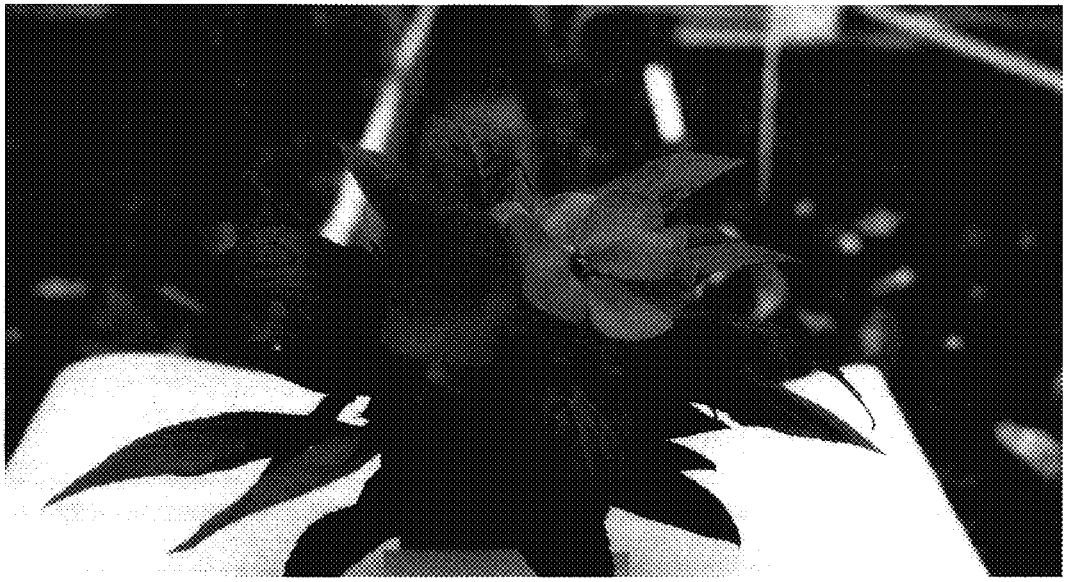

* * * * *